(12) United States Patent
Tanishima et al.

(10) Patent No.: US 8,576,079 B2
(45) Date of Patent: Nov. 5, 2013

(54) BIOLOGICAL INFORMATION MONITORING APPARATUS WITH PARTICULAR DISPLAY FEATURES

(75) Inventors: Masami Tanishima, Tokyo (JP); Hitoshi Inaba, Tokyo (JP); Katsumasa Imai, Tokyo (JP); Yoshihiro Takayanagi, Tokyo (JP); Masahiro Echigo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 448 days.

(21) Appl. No.: 12/899,653

(22) Filed: Oct. 7, 2010

(65) Prior Publication Data
US 2011/0080293 A1    Apr. 7, 2011

(30) Foreign Application Priority Data

Oct. 7, 2009 (JP) ................................ 2009-233753
Jul. 8, 2010 (JP) ................................ 2010-155911

(51) Int. Cl.
*G08B 21/00* (2006.01)
(52) U.S. Cl.
USPC ............. 340/573.1; 340/815.69; 340/539.12
(58) Field of Classification Search
USPC ........................... 340/539.11, 539.12, 539.1, 340/539.22–539.24, 573.1, 815.69
See application file for complete search history.

(56) References Cited

U.S. PATENT DOCUMENTS

| 2002/0032386 A1 | 3/2002 | Sackner et al. |
| 2003/0120164 A1 | 6/2003 | Nielsen et al. |
| 2007/0185429 A1 | 8/2007 | O'Mahony et al. |

FOREIGN PATENT DOCUMENTS

| JP | 64-68237 A | 3/1989 |
| JP | 2003-220045 A | 8/2003 |
| JP | 2007-188 A | 1/2007 |
| JP | 2007-90088 A | 4/2007 |
| WO | 01/39832 A1 | 6/2001 |

OTHER PUBLICATIONS

Extended European Search Report dated Jan. 14, 2011 for EP 10 18 6858.
Japanese Office Action and English translation to show relevance for the related Japanese Patent Application No. 2010-155911 dated Aug. 6, 2013.

*Primary Examiner* — Jeffery Hofsass
(74) *Attorney, Agent, or Firm* — Kenealy Vaidya LLP

(57) ABSTRACT

A biological information monitoring apparatus operable to receive biological information measured by a detector adapted to be attached to a patient, and operable to display the biological information on a display, includes: a first display controller which displays an alarm on the display; and a second display controller which displays, on the display, first information which responses to the displayed alarm.

18 Claims, 17 Drawing Sheets

FIG. 13

| | | | | |
|---|---|---|---|---|
| ICU-004 | | KOHDEN JIRO | | |
| RECORD | | | INTERRUPTION OF RADIO WAVE | |
| SETTING | | | | |
| 0BG005X6 2010 | HR --- | KOHDEN MATSUKO | | |
| RECORD | | | CHECK ELECTRODES | |
| SETTING | SpO2 --- | | | |
| 0BG005X6 4064 | HR --- | KOHDEN UMEKO | | |
| RECORD | | | CHECK ELECTRODES | |
| SETTING | SpO2 99 | | | |
| ICU-001 | HR --- | KOHDEN SABURO | | |
| RECORD | | | CHECK ELECTRODES | |
| SETTING | SpO2 --- | | | | ably obtained. The patent infringement "IS CLEAN AND THOROUGHLY
BIOLOGICAL INFORMATION MONITORING APPARATUS WITH PARTICULAR DISPLAY FEATURES

BACKGROUND OF THE INVENTION

The present invention relates to a biological information monitoring apparatus (so-called a bedside monitor or a central monitor) which receives biological information measured by a biological information detecting unit attached to the patient, directly from the biological information detecting unit or via a network, and which displays the biological information on a displaying unit, and particularly to a biological information monitoring apparatus which displays a vital alarm that is output in abnormality of the biological information, or a technical alarm that is output in abnormality of the biological information monitoring apparatus, a sensor, or the measurement environment, on a displaying unit, and which, after the vital alarm or the technical alarm is displayed, can display responding information that corresponds to the vital alarm or the technical alarm, on the displaying unit.

As a biological information monitoring apparatus which displays biological information that is obtained by processing a detection signal detected from a living body, on a displaying unit, JP-A-2003-220045 discloses a patient monitoring system which includes: a non-invasive cardiac output sensor being capable of acquiring a signal from a patient indicative of blood flow through a heart of the patient; a multi-lead electrocardiogram (ECG) sensor including a plurality of ECG electrodes capable of acquiring a plurality of ECG signals from the patient; and a patient monitor console including an analysis module being coupled to the non-invasive cardiac output sensor and to the multi-lead ECG sensor and processing the signal from the patient indicative of blood flow to produce a value pertaining to cardiac output, and a display being coupled to the analysis module and displaying the value pertaining to cardiac output and an ECG waveform generated based on the ECG signals.

The paragraph 0032 of JP-A-2003-220045 discloses as follows.

"A top level ICG menu 300 as shown in FIG. 4 is displayed. The top level. ICG menu 300 comprises a patient information button 302, a fast look button 304, a secondary parameters button 306, a limits button 308, a trends button 310, a help button 312, a waveform button 314, a speed button 316, a signal quality button 318, a beat average button 320, a change normals button 322, and a check leads button 324."

As an alarm for abnormality of a measured value, the paragraph 0039 of JP-A-2003-220045 discloses as follows.

"If an operator input is received selecting the limits button, then a limits menu is displayed. The limits menu permits the operator to adjust alarm limits for TFC and CI. High and low limits can be adjusted for both parameters. The current limit settings are shown in an information window, and the current value of that parameter for the monitored patent is also shown using arrows. As long as that value remains between the high and low limits, there will be no alarm. Should a limit be exceeded, an alarm will occur."

FIG. 8, which corresponds to FIG. 4 of JP-A-2003-220045, includes the help button 312 in a display screen. The paragraph 0041 of JP-A-2003-220045 discloses as follows.

"If the help button 312 is selected and an operator input is received, then the help information windows are displayed."

The help information window 370 of FIG. 9, which corresponds to FIG. 10 of JP-A-2003-220045, includes a display of "GETTING STARTED
CONFIRM ADEQUATE SKIN PREPARATION!
SHAVE HAIR AT SENSOR SITES.
MAKE SURE SKIN IS CLEAN AND THOROUGHLY DRY.
Orient ICG Sensors with Heart Designation Closest to the PATIENT'S HEART.
VERIFY ICG R and L CABLE BUNDLES CORRESPOND TO THE PATIENT'S ANATOMIC R AND L SIDES.
ENTER REQUIRED PATIENT INFO INCLUDING HEIGHT, WEIGHT, AGE AND SEX.
CONFIRM SOURCE FOR MAP, CVP, AND PAW VALUES VIA THE PATIENT INFO MENU.", and icons of "NEXT WINDOW" and "CLOSE WINDOW" are displayed in the help information window 370.

Moreover, the help information window 372 of FIG. 10, which corresponds to FIG. 11 of JP-A-2003-220045, includes a display, which includes the graphic illustration, of "PROPER SENSOR PLACEMENT
NECK: PLACE NECK SENSORS VERTICALLY ALONG THE SIDES OF THE NECK DIRECTLY BELOW THE EAR LOBE.
THORAX: PLACE THE SUPERIOR THORACIC SENSOR IN LINE WITH THE XIPHOID PROCESS ON EITHER SIDE OF THE THORAX ALONG THE MID-AXILLARY LINE.
SENSOR PAIRS MUST BE POSITIONED DIRECTLY OPPOSITE EACH OTHER.", and icons of "NEXT WINDOW", "PREVIOUS WINDOW", and "CLOSE WINDOW" are displayed in the help information window 372.

Furthermore, the help information window 374 of FIG. 11, which corresponds to FIG. 12 of JP-A-2003-220095, includes a display of "HELP FOR ICG MONITORING
PROBLEM: PARAMETER VALUE DISPLAYS X.
SOLUTIONS: VERIFY PATIENT INFO HAS BEEN ENTERED, INCLUDING HEIGHT, WEIGHT, AGE, SEX, A SOURCE FOR MAP AND VALUES FOR CVP AND PAW.
PARAMETER INPUT VALUES MAY BE OUT OF RANGE.
PROBLEM: POOR SIGNAL QUALITY
SOLUTIONS: MINIMIZE PATIENT MOVEMENT AND TALKING AS THEY MAY AFFECT DATA QUALITY.
CHECK ICG LEAD INTEGRITY INCLUDING SENSOR GEL AND CABLE CONNECTIONS.
SELECT A SIGNAL QUALITY OPTION THAT DISPLAYS THE BEST WAVEFORM AND SIGNAL STRENGTH INDICATORS.", and icons of "NEXT WINDOW" and "CLOSE WINDOW" are displayed in the help information window 374.

In the patient monitoring system disclosed in JP-A-2003-220045, in response to an alarm for abnormality of a measured value and selection of the help button in the display screen, the help information window is displayed on the screen. The help information window is displayed in a so-called wizard format in which the user selects one of the icons of "NEXT WINDOW", "PREVIOUS WINDOW", and "CLOSE WINDOW" to select a display screen desired by the user. A close relationship is not established between the alarm generated by abnormality of the measured value or the like and the help information window displayed on the screen.

A biological information monitoring apparatus has a function of, as an alarm for abnormality occurring in a detection signal detected from the living body of the patient by the apparatus, the apparatus body unit, a sensor attached to the patient, or the like, generating a visual and/or auditory alarm. However, the alarm indicates only the present situation, and the apparatus does not generate a message in which the past alarm generating situation is considered, and which is different from the alarm.

As abnormality occurring in the body unit of the biological information monitoring apparatus or a sensor attached to the patient, in, for example, an SpO2 probe or ECG electrode which is a sensor, particularly, there sometimes occurs a phenomenon such as that, when the patient moves because of rolling over during measurement, the contact state is temporarily impaired, or that, after the sensor is once detached, the sensor is immediately returned to its original state. As abnormality in the measurement environment, for example, there are a state where, when a measured biological signal is wirelessly transmitted, an interruption of the radio wave or a failure of reception occurs, and a phenomenon in which the contact impedance of an electrode is increased and noises enter the signal.

Also in such a case, it is detected that abnormality occurs in the body unit of the apparatus, the sensor, or the measurement environment, and a visual and/or auditory alarm is generated as a technical alarm.

In the case where the contact state is temporarily impaired when the patient rolls over during measurement, or, after the sensor is once detached, the sensor is immediately returned to its original state, however, it is not always necessary that a medical person who monitors the patient through the biological information monitoring apparatus in a nurse's station goes to a medical ward of the patient, but the case where the contact state is temporarily impaired or detachment temporarily occurs cannot be distinguished from that where the sensor state is immediately returned to its original state.

According to improvement of the medical technology and advancement of medical equipment, a medical person is requested not only to have extensive knowledge but also to rapidly respond to an alarm. It can be assumed that, when an alarm is generated, an inexperienced medical person cannot decide how to respond to the alarm, or cannot know the cause of the alarm.

SUMMARY

It is therefore an object of the invention to provide a biological information monitoring apparatus which displays a vital alarm that is output in abnormality of a detection signal, or a technical alarm that is output in abnormality of the biological information monitoring apparatus, a sensor, or the measurement environment, on a displaying unit, and which, after the vital alarm or the technical alarm is displayed, displays responding information that corresponds to the vital alarm or the technical alarm, on the displaying unit.

It is also an object of the invention to provide a biological information monitoring apparatus which, when a vital alarm that is output in abnormality of a detection signal, or a technical alarm that is output in abnormality of the biological information monitoring apparatus, a sensor, or the measurement environment is displayed on a displaying unit, can output responding information in which a situation where a vital alarm or a technical alarm is generated in past is considered.

Examples of the abnormality of the measurement environment are a state where, when measured biological information is wirelessly transmitted to the biological information monitoring apparatus, the apparatus cannot receive the biological information because of an interruption of the radio wave or a failure of reception, and that where the attachment state of an electrode attached to a living body is poor.

In order to achieve the object, according to the invention, there is provided a biological, information monitoring apparatus operable to receive biological information measured by a detector adapted to be attached to a patient, and operable to display the biological information on a display, the biological information monitoring apparatus comprising: a first display controller which displays an alarm on the display; and a second display controller which displays, on the display, first information which responses to the displayed alarm.

The first information may include means, instruction, or suggestion for canceling abnormality related to the displayed alarm.

The alarm and the first information may be not superimposed on each other on the display.

The first information may include at least one of a character and a graphical illustration.

When the first information is displayed on the display, a sound may be output.

When the displayed alarm satisfies at least one of predetermined conditions of a generation frequency, a generation number, a duration time, and an integration time, the first information may be displayed on the display.

When a predetermined condition is satisfied, the first information may be displayed, and when the predetermined condition is unsatisfied after the first information is displayed, display of the first information may be cancelled.

When a condition is satisfied, the first information may be displayed, and the condition may be set for kind of the alarm.

The first information may be displayed in a blinking or inverted manner.

The first information may be displayed when a user operates a guide key, which is displayed on the display at a time when the alarm is displayed, which is displayed on the display after a predetermined time elapses from a time when the alarm is displayed, or which is displayed on the display when a number of the alarm reaches a predetermined number.

When a user selects the alarm displayed on the display, the first information may be displayed on the display.

The first information may be formed by a window including a plurality of elements, and one of the plurality of elements which corresponds to the displayed alarm may be displayed at a most front.

When the alarm satisfies at least one of predetermined conditions of a generation frequency, a generation number, a duration time, and an integration time, the second display controller may display, on the display, second information which responses to the alarm and which a user can operate.

The second information may include a plurality of information.

The second display controller may determine the second information to be displayed, based on presence or absence of the biological information to be measured.

The alarm may include at least one of a vital alarm that is output in abnormality of the biological information and a technical alarm that is output in abnormality of the biological information monitoring apparatus, the detector, or measurement environment.

BRIEF DESCRIPTION OF THE DRAWINGS

FIG. 13 is a view showing contents displayed on the displaying unit of the biological information monitoring apparatus, before a pop-up navigation in the invention is displayed.

DETAILED DESCRIPTION OF EMBODIMENTS

A configuration related to a first example of responding information (hereinafter, referred to as action message) in the invention will be described with reference to FIG. 1.

Figure 1:
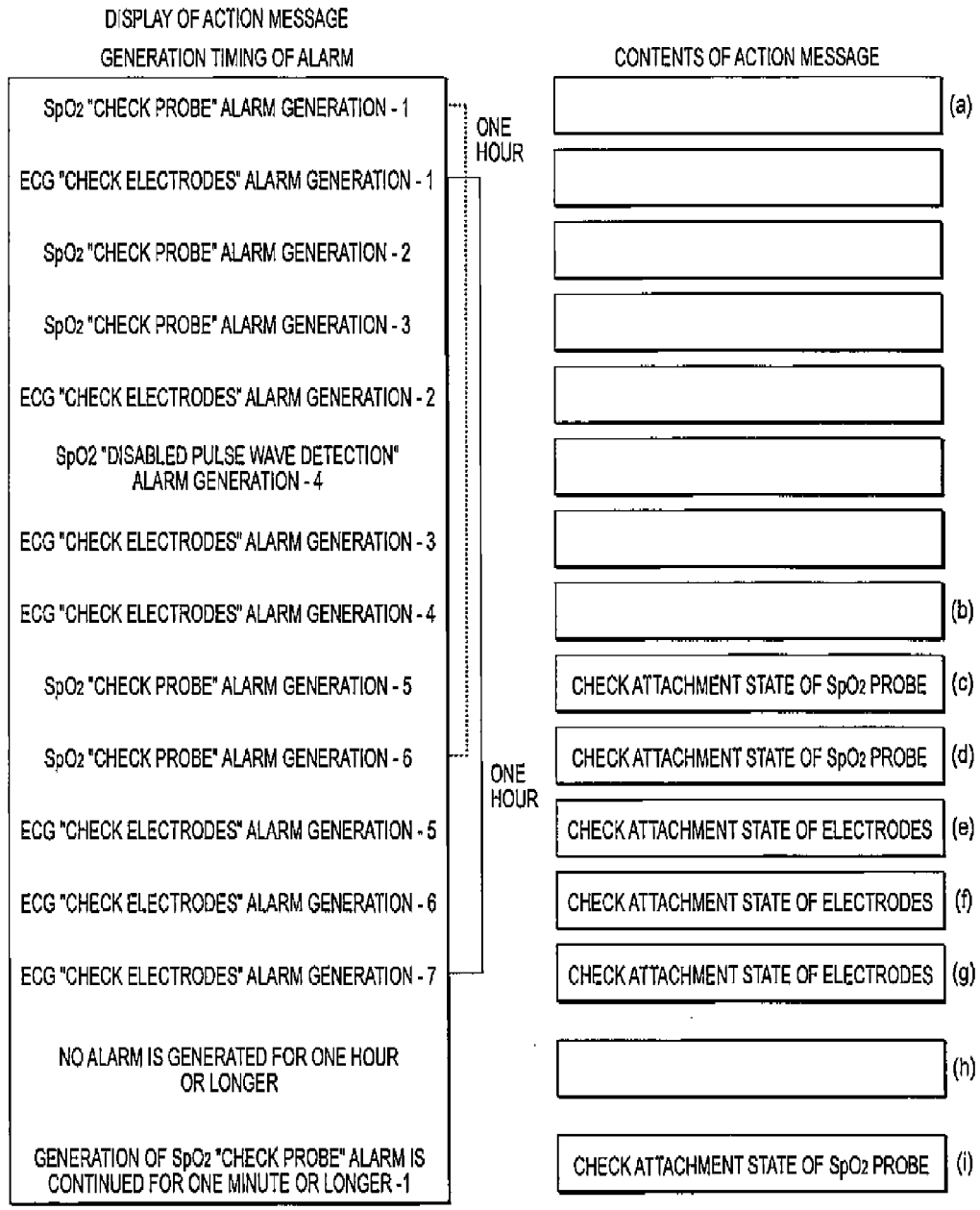
FIG. 1 is a view illustrating relationships between generation timings of alarms and action messages in the biological information monitoring apparatus of the invention.

FIG. 1 is a view illustrating relationships between generation timings of alarms and action messages in the biological information monitoring apparatus. In the biological information monitoring apparatus, at least one of a vital alarm that is output in abnormality of a detection signal detected from the patient and a technical alarm that is output in abnormality of the biological information monitoring apparatus, a sensor, or the measurement environment is displayed on a displaying unit by an alarm display controlling unit, and the first example of the responding information in which a situation where a vital alarm or a technical alarm is generated in past is considered is displayed on the displaying unit by a responding information display controlling unit.

The left side of FIG. 1 shows generation timings of technical alarms related the SpO2 and the ECG of one patient in the biological information monitoring apparatus.

Each time when one of the illustrated technical alarms is generated, visual alarms such as "CHECK PROBE", "CHECK ELECTRODES", "DISABLED PULSE WAVE DETECTION", or the like is displayed in a display area for this patient of the biological information monitoring apparatus, and also an auditory alarm is generated as required.

In this state, however, it is impossible to distinguish whether this state is caused by a case where, when the patient moves because of rolling over during measurement, the contact state is temporarily impaired, or the sensor is temporarily detached, or that where, after the contact state is temporarily impaired or the sensor is once detached, the sensor is returned to its normal state by the motion of the patient.

In the biological information monitoring apparatus, in the case where a technical alarm such as those shown in the left side of FIG. 1 is generated, an action message is displayed in response to the next operation, in the display area for this patient of the biological information monitoring apparatus.

Condition for displaying an action message based on the generation frequency, the generation number, the duration time, the integration time, and the like of the technical alarms shown in FIG. 1 is that any one of cases where the accumulated generation number of individual alarms within one hour is five, and where the same alarm is continued for one minute is satisfied (the condition is not always restricted to this, and can be adequately set).

Before the accumulated generation number of technical alarms related to the SpO2 or the ECG for one hour reaches five, an action message is not displayed in the display area for this patient of the biological information monitoring apparatus as shown in (a) to (b) in the right side of FIG. 1.

At the timing when the accumulated generation number of technical alarms related to the SpO2 for one hour reaches five, as shown in (c) in the right side of FIG. 1, an action message of "CHECK ATTACHMENT STATE OF SpO2 PROBE" which corresponds to the generated technical alarm is displayed in the display area for this patient of the biological information monitoring apparatus. When the action message is displayed, a sound for the action message may be produced.

In the case where an alarm sound for the technical alarm is generated, the sound for the action message which is generated when the action message is displayed is preferably different from the alarm sound.

The action message which is displayed in this case is requested to instruct/suggest a medical person to expedite the check of the SpO2 probe so as to escape from the state of the generated technical alarm (to cancel the state of the generated technical alarm), and a more specific one such as "AGAIN ATTACH SpO2 PROBE" or "REPLACE TAPE OF SpO2 PROBE" may be more preferable. The action massage may provide the medical person with means for canceling the state of the generated technical alarm.

Therefore, even an inexperienced medical person can easily know an action to deal with the generated technical alarm, and hence the work efficiency can be improved.

Next, also at the timing when the accumulated generation number of technical alarms related to the SpO2 for one hour reaches six, as shown in (d) in the right side of FIG. 1, the action message of "CHECK ATTACHMENT STATE OF SpO2 PROBE" is successively displayed in the display area for this patient of the biological information monitoring apparatus.

In the case where, after the accumulated generation number of technical alarms related to the SpO2 for one hour reaches six, a further technical alarm related to the SpO2 is not generated within one hour from the second generation timing of "CHECK PROBE", the condition that the accumulated generation number within one hour is five is not satisfied, the action message of "CHECK ATTACHMENT STATE OF SpO2 PROBE" is not displayed in the display area for this patient of the biological information monitoring apparatus. This state is not shown in the figures.

Next, at the timing when the accumulated generation number of technical alarms of "CHECK ELECTRODES" related to the ECG for one hour reaches five, as shown in (e) in the right side of FIG. 1, an action message of "CHECK ATTACHMENT STATE OF ELECTRODES" is displayed in the display area for this patient of the biological information monitoring apparatus.

In a similar manner as described above, the action message displayed in this case is requested to instruct/suggest a medical person to expedite the check of the ECG electrodes so as to cancel the state of the generated technical alarm, and a more specific one such as "ATTACH NEW ELECTRODES" or "CHANGE ATTACH POSITIONS OF ELECTRODES" may be more preferable.

Next, also at the timing when the accumulated generation number of technical alarms related to the ECG for one hour reaches six, as shown in (f) in the right side of FIG. 1, the action message of "CHECK ATTACHMENT STATE OF ELECTRODES" is successively displayed in the display area for this patient of the biological information monitoring apparatus.

Next, also at the timing when the accumulated generation number of technical alarms related to the ECG for one hour reaches seven, as shown in (g) in the right side of FIG. 1, the action message of "CHECK ATTACHMENT STATE OF ELECTRODES" is successively displayed in the display area for this patient of the biological information monitoring apparatus.

When a technical alarm related to the SpO2 or the ECG is not generated for one hour or longer, an action message is not displayed in the display area for this patient of the biological information monitoring apparatus as shown in (h) in the right side of FIG. 1.

In the case where a technical alarm of "CHECK PROBE" related to the SpO2 continues for one minute or longer, as shown in (i) in the right side of FIG. 1, an action message of "CHECK ATTACHMENT STATE OF SpO2 PROBE" is displayed in the display area for this patient of the biological information monitoring apparatus.

In the biological information monitoring apparatus, when a technical alarm that is output in abnormality of the biological information monitoring apparatus or a sensor is displayed on a displaying unit, as described above, it is possible to output an action message in which a situation where a technical alarm is generated in past is considered. Therefore, it is possible to distinguish whether this state is caused by a case where, when the patient moves because of rolling over during measurement, the contact state of the sensor (probe, electrodes, or the like) is temporarily impaired, or the sensor is temporarily detached, or that where the sensor is immediately returned to its normal state. Consequently, a medical person who monitors the patient through the biological information monitoring apparatus in a nurse's station can adequately respond to the alarm.

Although, in the above, the description is made with respect to a technical alarm that is output in abnormality of the biological information monitoring apparatus or a sensor, it is a matter of course that the invention can be applied also to a vital alarm that is output in abnormality of a detection value of biological information of the patient or a value which is obtained by processing the detection value.

Although, in the above, the description is made with respect to "action message" which is displayed in characters, the display manner is not limited to a character display but may use also another display mode such as graphics, graphs, or photographs.

The display screen of an action message is displayed on the displaying unit in a display mode in which the action message is not superimposed on an alarm display. This is preferable because the alarm display is not disturbed.

In the display of an action message on the displaying unit, a display mode which is intended to attract the attention of a medical person may be employed such as that a plurality of levels are set as conditions for displaying the action message, and a visual display such as different colors, a blinking display, or an inverted display is used in accordance with the preset one of the plurality of levels.

Figure 12:
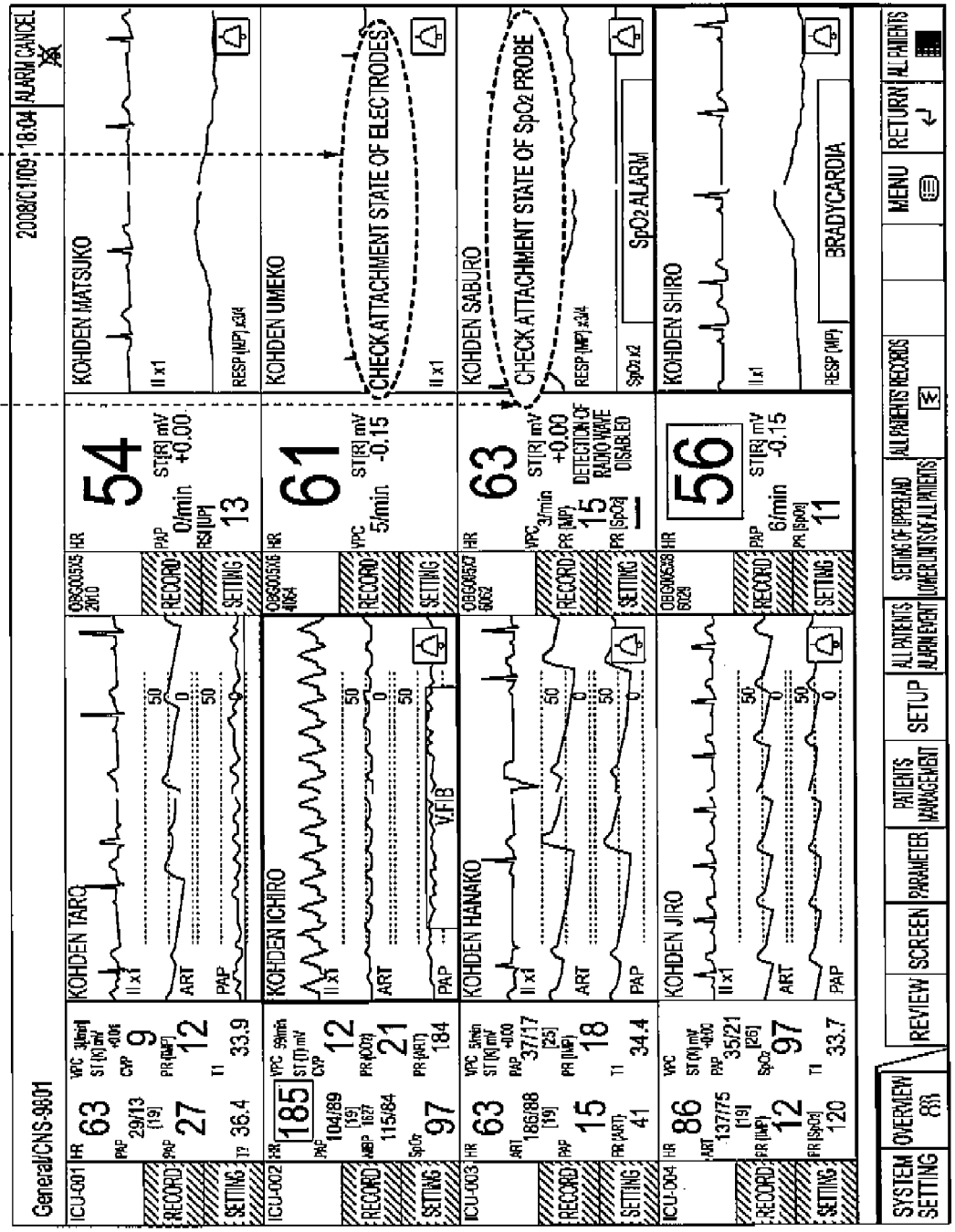
FIG. 12 is a view showing contents displayed on the displaying unit of the biological information monitoring apparatus, in the case where an action message in the invention is displayed.

FIG. 12 shows an example of the display of an action message in a biological information monitoring apparatus (so-called a central monitor) which is placed in a nurse's station or the like, and in which biological signals of a plurality of patients can be simultaneously monitored.

As described above, with respect to the first example of the responding information, a medical person can automatically obtain responding information corresponding to the generated alarm, without performing a special operation.

Next, a configuration related to a second example of responding information (hereinafter, referred to as guide screen) in the invention will be described.

An example in which a guide function including the guide screen is added will be described with reference to FIGS. 2 to 5. In the biological information monitoring apparatus, after at least one of a vital alarm that is output in abnormality of the detection signal detected from the patient and a technical alarm that is output in abnormality of the biological information monitoring apparatus, the sensor, or the measurement environment is displayed on the displaying unit by the alarm display controlling unit, the guide screen is displayed by the responding information display controlling unit for facilitating a medical person to respond to the alarm.

Figure 2:
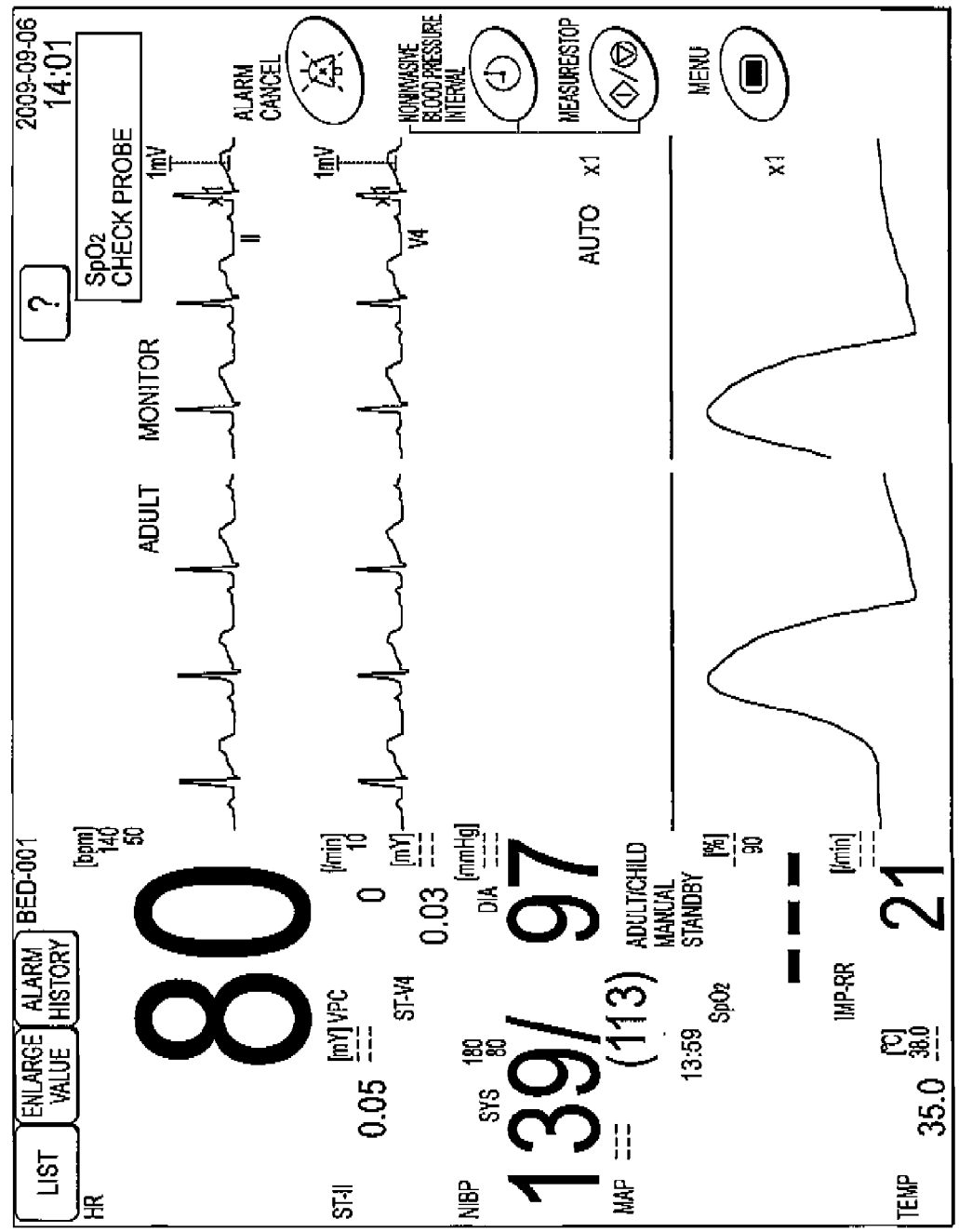
FIG. 2 is a view illustrating a relationship between a technical alarm of "CHECK SpO2 PROBE" and a guide button (guide key) which are displayed on a displaying unit of the biological information monitoring apparatus of the invention.

FIG. 2 shows a state where, in the biological information monitoring apparatus, a visual alarm of "CHECK SpO2 PROBE" which is an alarm related to the SpO2 that is one of the technical alarms shown in the right side of FIG. 1 is displayed in a part (in FIG. 2, an upper right part) of the display area for this patient of the biological information monitoring apparatus.

In the display area in FIG. 2, a waveform of a detection signal detected from the living body of the patient, and biological information that is obtained by processing the detection signal are displayed.

In the display area in FIG. 2, a question mark button (hereinafter, referred to as guide key) is displayed above the display of "CHECK SpO2 PROBE".

Figure 3:
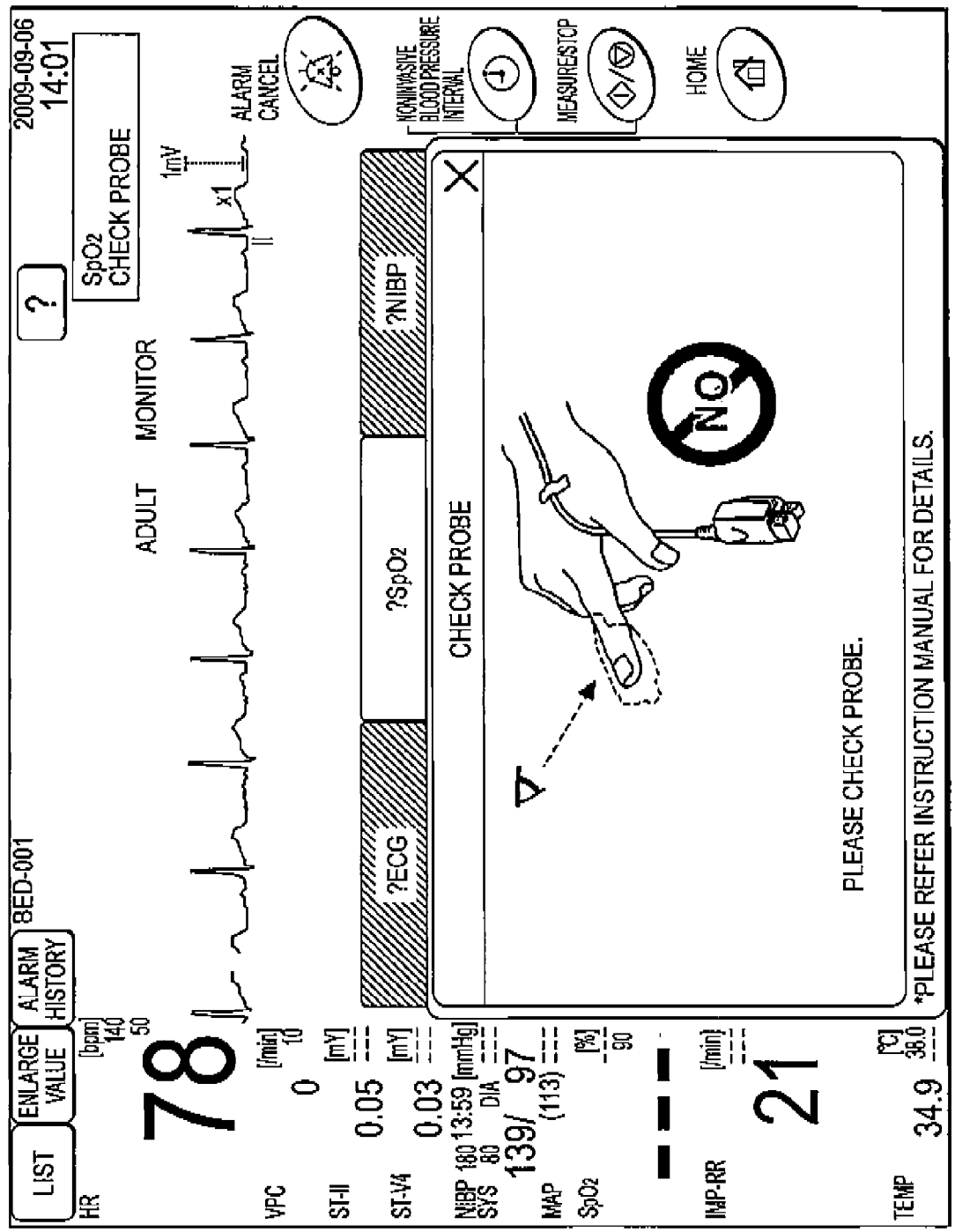
FIG. 3 is a view showing contents displayed on the displaying unit of the biological information monitoring apparatus, in the case where the guide key is selected in the state of FIG. 2.

When a medical person selects (clicks) the guide key in this state, the display screen of the biological information monitoring apparatus is changed to the state of FIG. 3.

In FIG. 3, guide information corresponding to "CHECK SpO2 PROBE" is displayed with graphic illustration on the guide screen while being partly superimposed on the display screen of the waveform detected from the living body, and biological information that is obtained by processing the detection signal.

When the guide information is displayed, a sound may be produced. In the case where an alarm sound for the technical alarm is generated, the sound for the guide information which is generated when the guide information is displayed is preferably different from the alarm sound.

By the graphically illustrated guide information of FIG. 3, a medical person can be provided with optimum responding information with respect to the technical alarm of "CHECK SpO2 PROBE". It can be said that, for an inexperienced medical person, this information is beneficial information.

In place of displaying the guide key, the display may be changed to the state of FIG. 3 by an operation in which "the user selects the displayed alarm". The terms "the user selects the displayed alarm" means that the user selects (clicks) "CHECK SpO2 PROBE" in the display screen of FIG. 2.

Figure 4:
FIG. 4 is a view illustrating a relationship between a technical alarm of "DISCONNECTION OF SpO2 CONNECTOR" and a guide button (guide key) which are displayed on the displaying unit of the biological information monitoring apparatus of the invention.

In the display area of the biological information monitoring apparatus shown in FIG. 4, a waveform of a detection signal detected from the living body of the patient, and biological information that is obtained by processing the detection signal are displayed.

In the display area in FIG. 4, a guide key is displayed above the display of a technical alarm of "DISCONNECTION OF SpO2 CONNECTOR".

Figure 5:
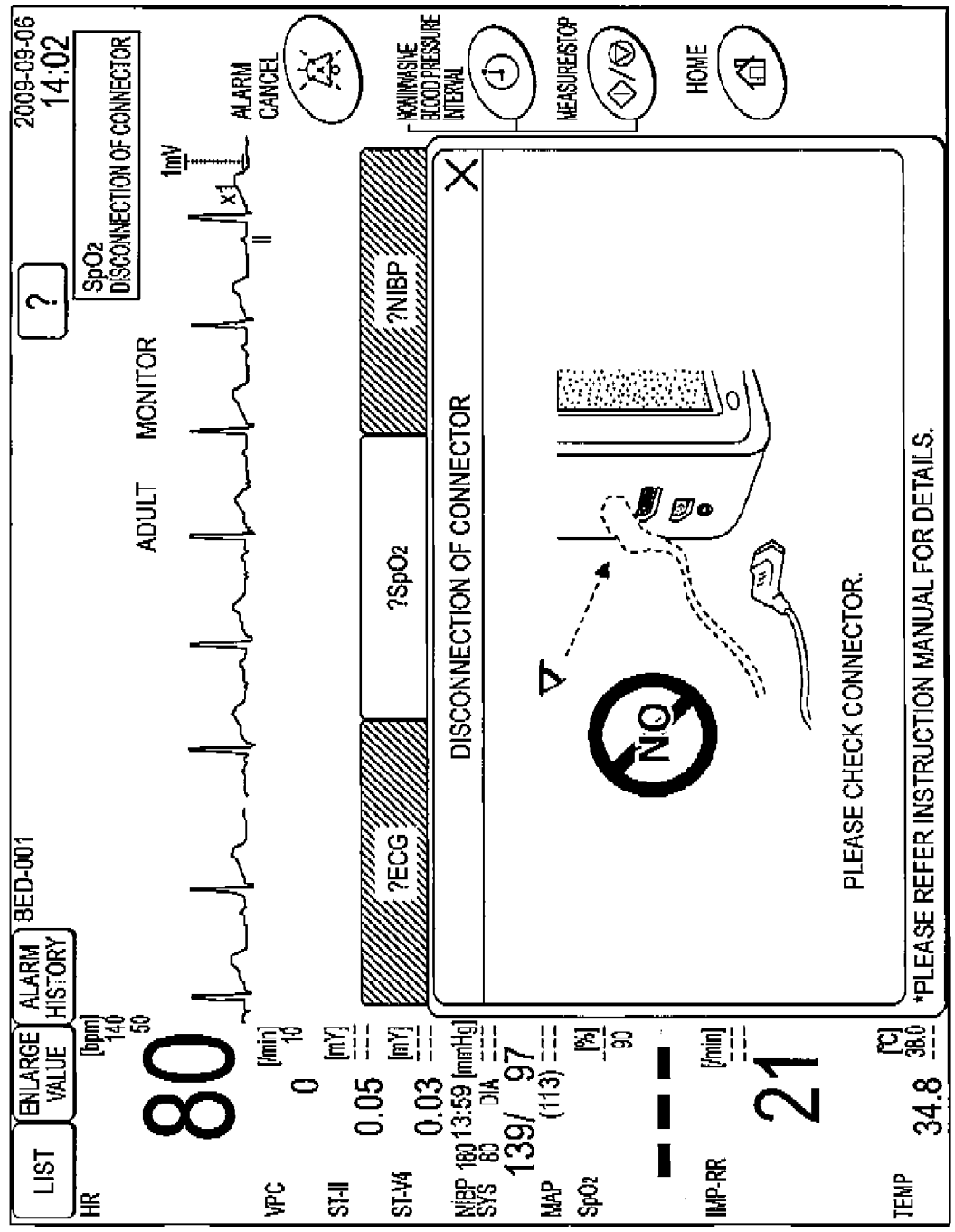
FIG. 5 is a view showing contents displayed on the displaying unit of the biological information monitoring apparatus, in the case where the guide key is selected in the state of FIG. 4.

When a medical person selects (clicks) the guide key in this state, the display screen of the biological information monitoring apparatus is changed to the state of FIG. 5.

In FIG. 5, guide information corresponding to "DISCONNECTION OF SpO2 CONNECTOR" is displayed with graphic illustration on the guide screen while being partly superimposed on the display screen of the waveform detected from the living body of the patient, and biological information that is obtained by processing the detection signal.

By the graphically illustrated guide information of FIG. 5, a medical person can be provided with optimum responding information with respect to the technical alarm of "DISCONNECTION OF SpO2 CONNECTOR".

Similarly with the case of the first example of the responding information, preferably, the displayed guide screen is displayed so as not to be superimposed on an alarm which has been already displayed.

In the case where the guide screen is a dialog window configured by a plurality of pages such as shown in FIGS. 3 and 5, it is preferred that the page (?SpO2) corresponding to the displayed alarm is displayed in the most front face.

In the examples of FIGS. 2 to 5, by a selection (click) of a guide key which is displayed at the same time when a technical alarm such as "CHECK SpO2 PROBE" or "DISCONNECTION OF SpO2 CONNECTOR" is generated on the display screen, or when a predetermined time elapses or a predetermined number reaches, guide information corresponding to "CHECK SpO2 PROBE" or "DISCONNECTION OF SpO2 CONNECTOR" is displayed with graphic illustration on the guide screen while being partly superimposed on the display screen of the waveform detected from the living body of the patient, and biological information that is obtained by processing the detection signal. Examples in which a guide screen is displayed in another procedure will be described.

Figure 6:
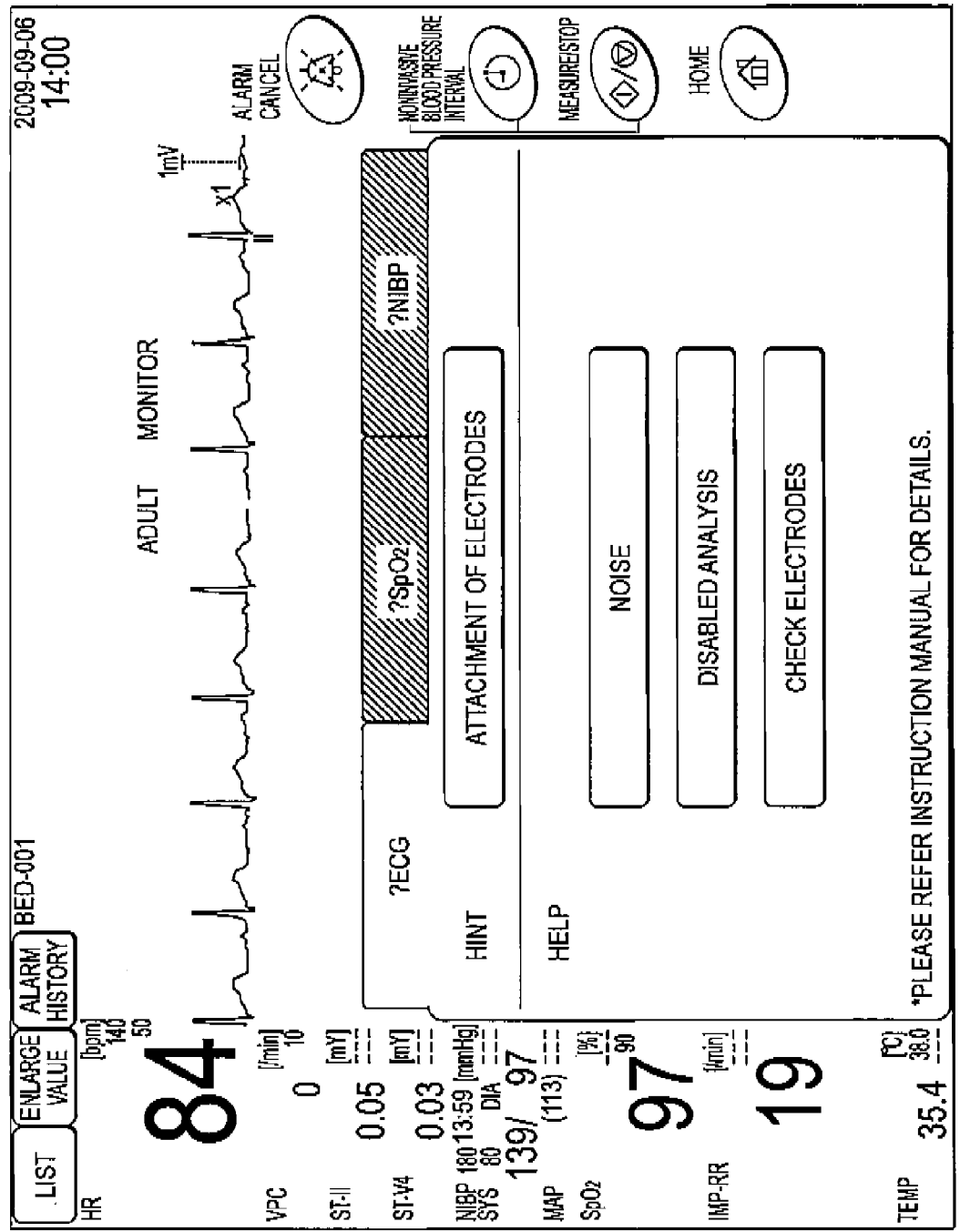
FIG. 6 is a view showing a display example of a guide screen in the case where, on a screen displaying a waveform of a detection signal detected from the living body of the patient and biological information that is obtained by processing the detection signal in a displaying area of the biological information monitoring apparatus, a guide button which is displayed in a menu screen after a menu button is selected (clicked).

FIG. 6 shows a display example of a guide screen in the case where a guide button which is displayed on a menu screen after a menu button is selected (clicked) on a screen on which the waveform detected from the living body of the patient, and biological information that is obtained by processing the detection signal are displayed in the display area of the biological information monitoring apparatus.

FIG. 6 shows an example of the screen in the case where the guide button which is displayed on the menu screen is selected (clicked). In the screen, there are files respectively for the ECG, the SpO2, and the NIBP. The figure shows the state where the ECG file is selected.

In this state, on the screen, "ATTACHMENT OF ELECTRODES" is displayed as "HINT" item, and "NOISES", "DISABLED ANALYSIS", and "CHECK ELECTRODES" are displayed as "HELP" items.

Figure 7:
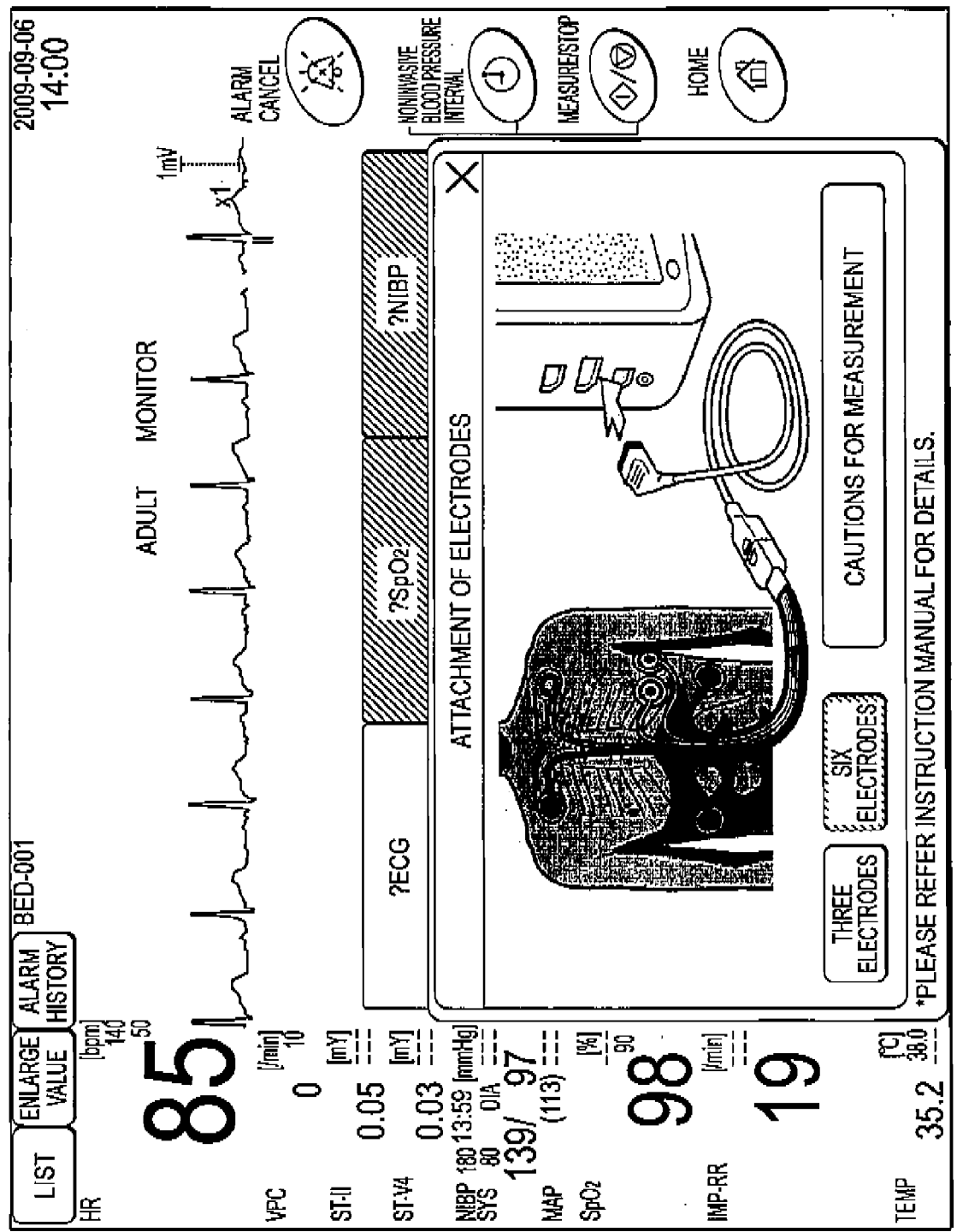
FIG. 7 is a view showing contents displayed on the displaying unit of the biological information monitoring apparatus, in the case where "CHECK ELECTRODES" button is selected in the state of FIG. 6.
Figure 8:
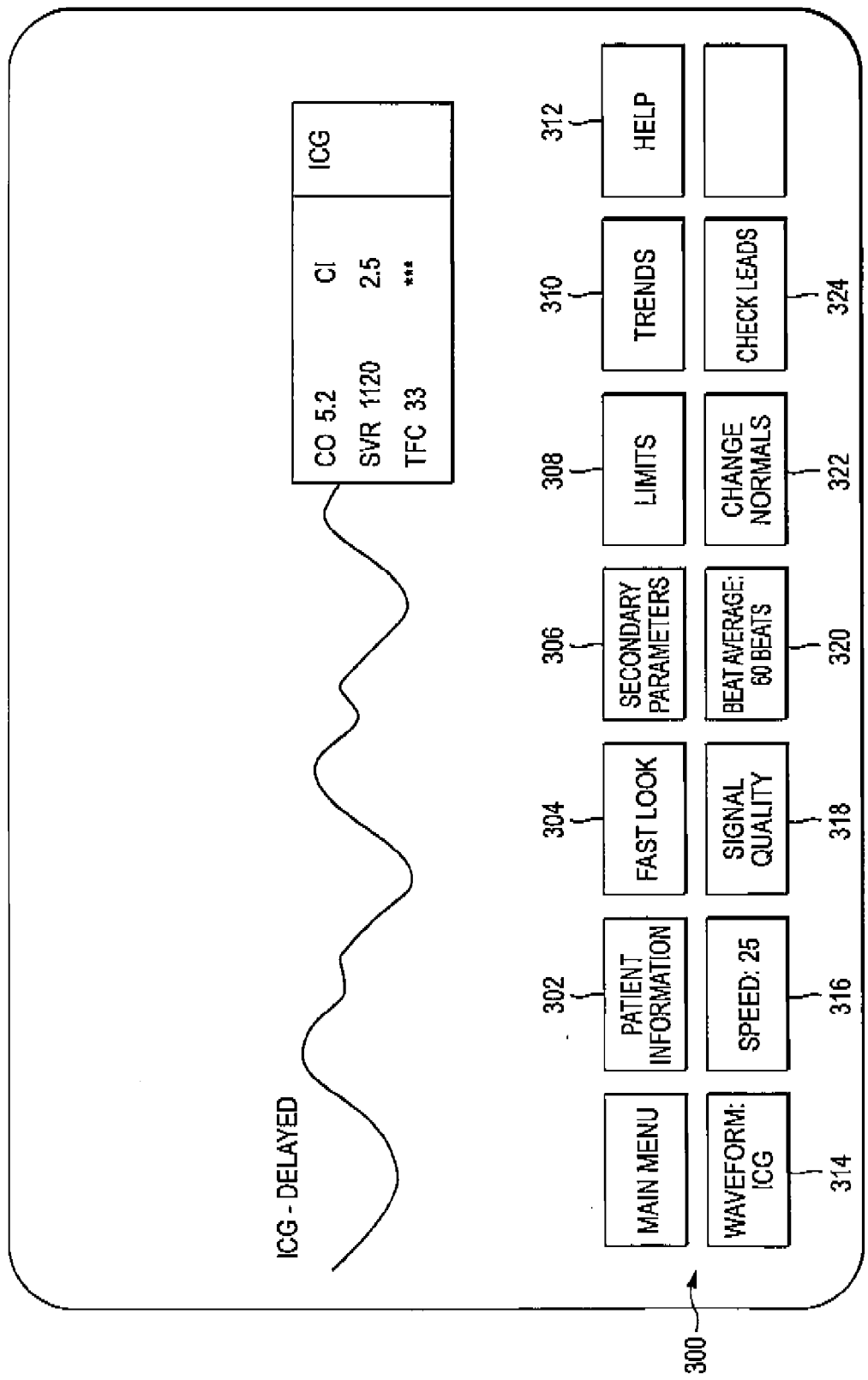
FIG. 8 is a view showing a situation where, on a screen displaying a waveform of a detection signal detected from the living body of the patient and biological information that is obtained by processing the detection signal in a displaying area of a biological information monitoring apparatus, a help button is displayed.
Figure 9:
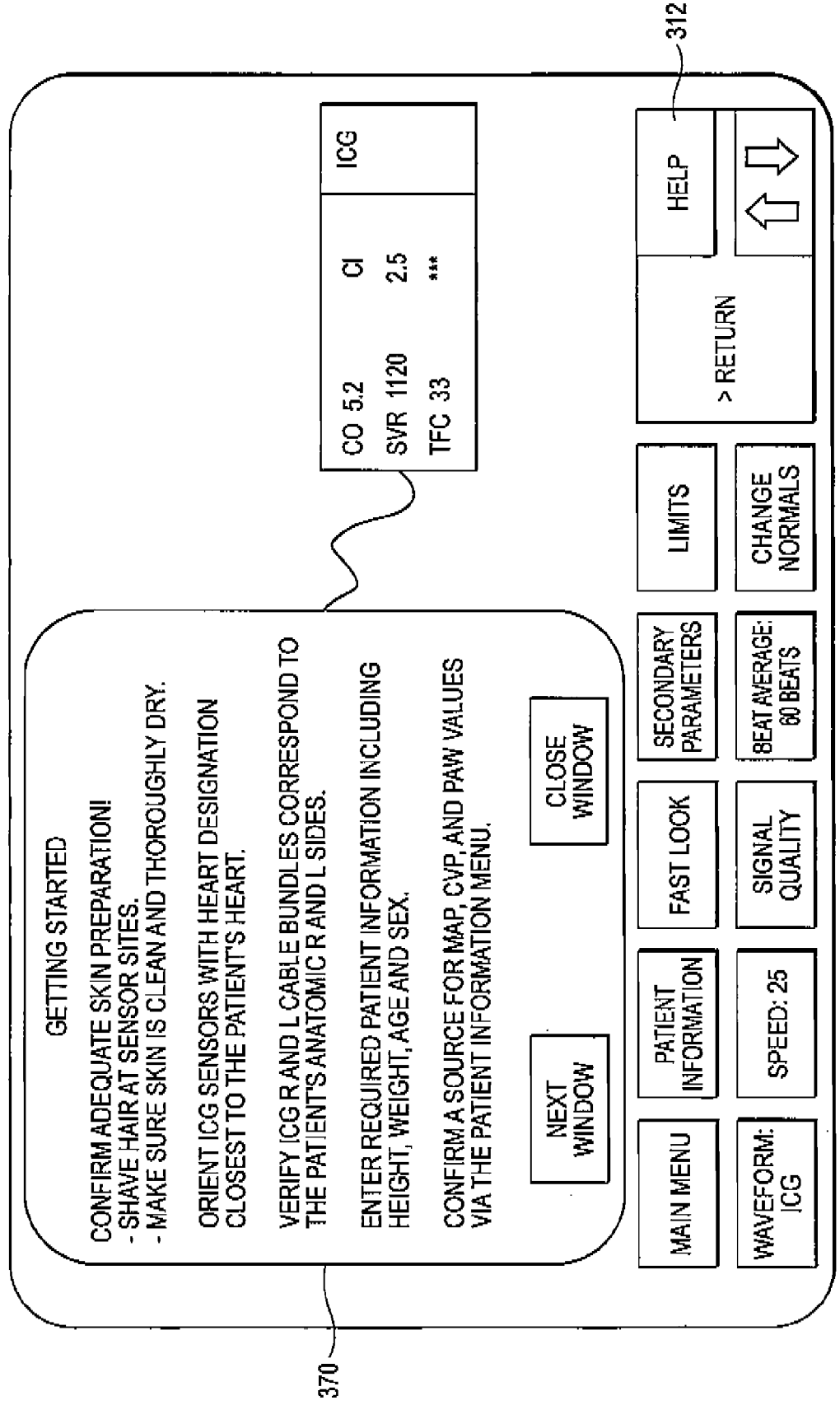
FIG. 9 is a view showing contents displayed on the displaying unit of the biological information monitoring apparatus, in the case where the help button is selected in the state of FIG. 8.
Figure 10:
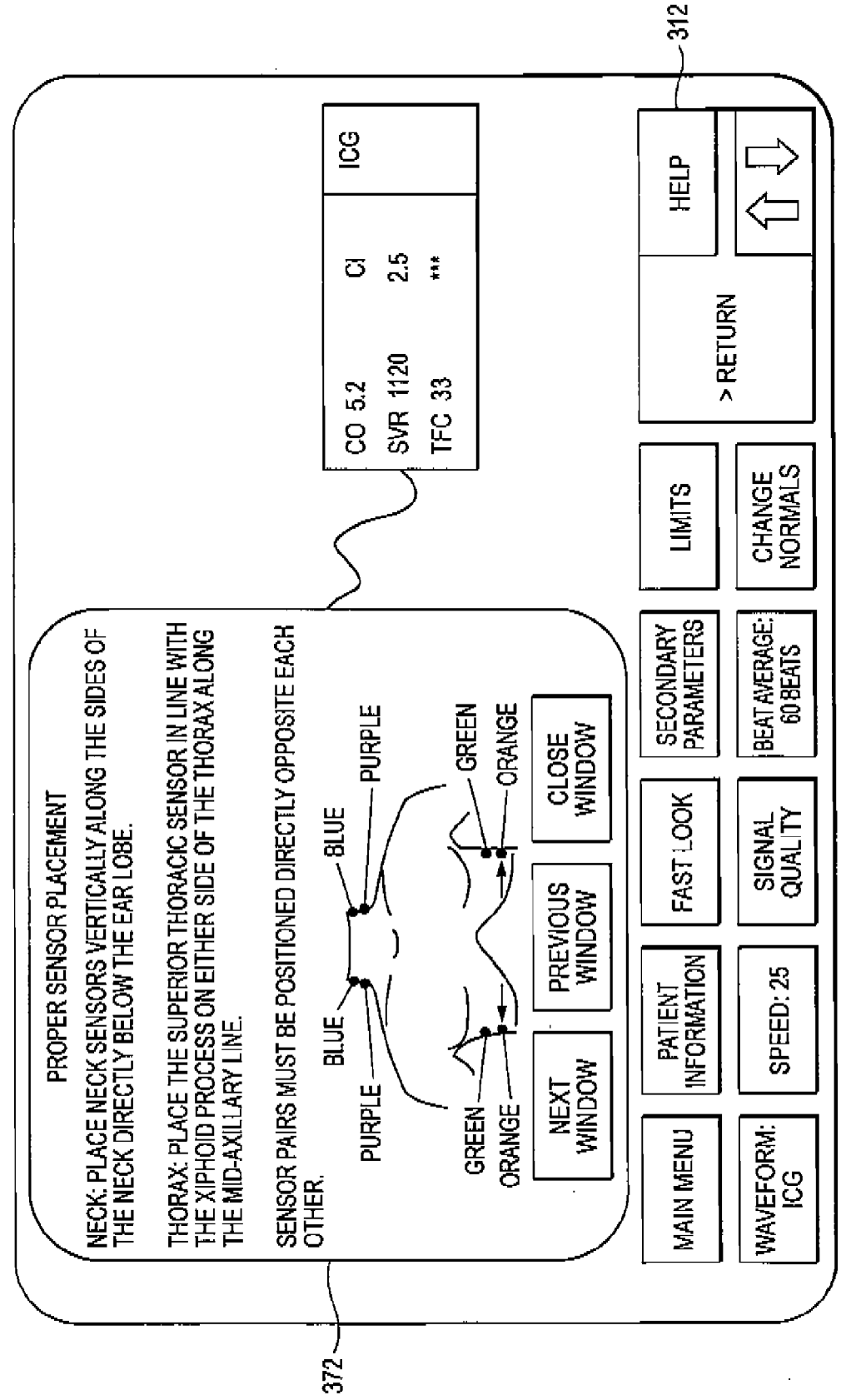
FIG. 10 is a view showing contents displayed on the displaying unit of the biological information monitoring apparatus, in the case where an up-arrow displayed below the help button is selected in the state of FIG. 9.
Figure 11:
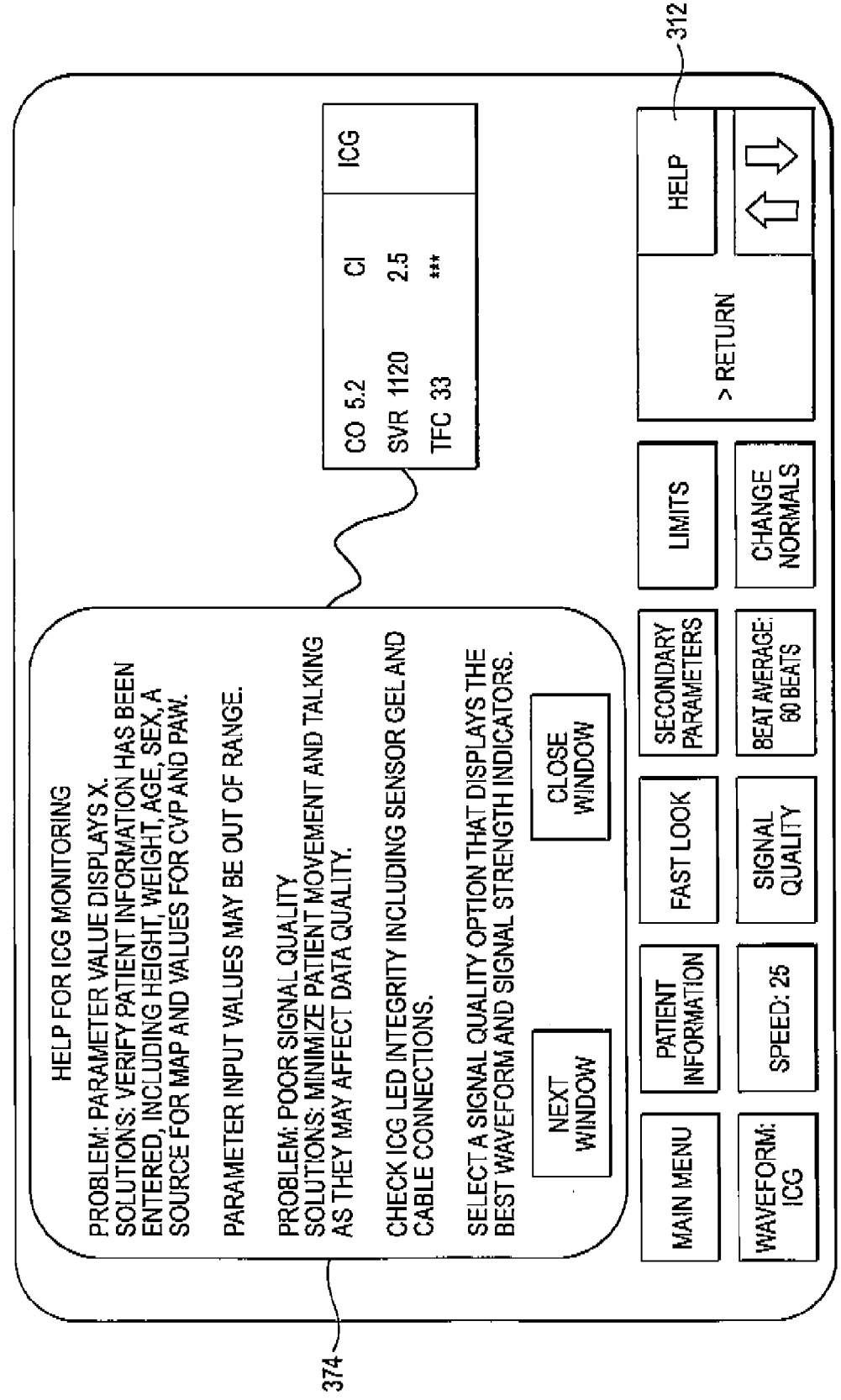
FIG. 11 is a view showing contents displayed on the displaying unit of the biological information monitoring apparatus, in the case where an up-arrow displayed below the help button is further selected in the state of FIG. 10.

When "CHECK ELECTRODES" button is selected (clicked) in this state, the display screen of the biological information monitoring apparatus is changed to the state of FIG. 7.

In FIG. 7, guide information corresponding to "CHECK ELECTRODES" of ECG is displayed with graphic illustration on the guide screen while being partly superimposed on the display screen of the waveform detected from the living body, and biological information that is obtained by processing the detection signal.

By the graphically illustrated guide information of FIG. 7, a medical person can be provided with optimum responding information with respect to the technical alarm of "CHECK ELECTRODES" of the ECG.

In the descriptions of FIGS. 2 to 7, guide information corresponding to the technical alarm such as "CHECK PROBE" of the SpO2, "CHECK ELECTRODES" of the ECG, or the like on the display screen of the waveform detected from the living body, and biological information that is obtained by processing the detection signal is produced. Alternatively, guide information corresponding to the action message such as "CHECK SpO2 PROBE" or "CHECK ECG ELECTRODES" shown in FIG. 1 may be displayed.

In the descriptions of FIGS. 2 to 7, guide information corresponding to the technical alarm such as "CHECK PROBE" of the SpO2, "CHECK ELECTRODES" of the ECG, or the like on the display screen of the waveform detected from the living body, and biological information that is obtained by processing the detection signal is produced. Alternatively, guide information corresponding to a vital alarm which is displayed in abnormality of a detection value of biological information detected from the patient or data which are obtained by processing the detection value may be displayed.

As described above, with respect to the second example of the responding information in the invention, a medical person is enabled to spontaneously obtain responding information corresponding to the generated alarm, by an operation which is performed by the medical person itself.

Next, a configuration related to a third example of responding information (hereinafter, referred to as pop-up navigation) in the invention will be described.

An example in which a pop-up navigation function including the pop-up navigation is added will be described with reference to FIGS. 13 and 14. In the biological information monitoring apparatus, when at least one of a vital alarm that is output in abnormality of the detection signal detected from the patient on the displaying unit by the alarm display controlling unit and a technical alarm that is output in abnormality of the biological information monitoring apparatus, the sensor, or the measurement environment on the displaying unit by the alarm display controlling unit, satisfies predetermined conditions, the pop-up navigation is displayed on the displaying unit by the responding information display controlling unit for instructing or suggesting an operation which is required by the user.

FIG. 13 shows a state where an alarm of "INTERRUPTION OF RADIO WAVE" is generated for KOHDEN Jiro, which is one of the patients, "CHECK ELECTRODES" is generated for KOHDEN Matsuko, which is one of the patients, "CHECK ELECTRODES" is generated for KOHDEN Umeko, which is one of the patients, and "CHECK ELECTRODES" is generated for KOHDEN Saburo, which is one of the patients.

Figure 14:
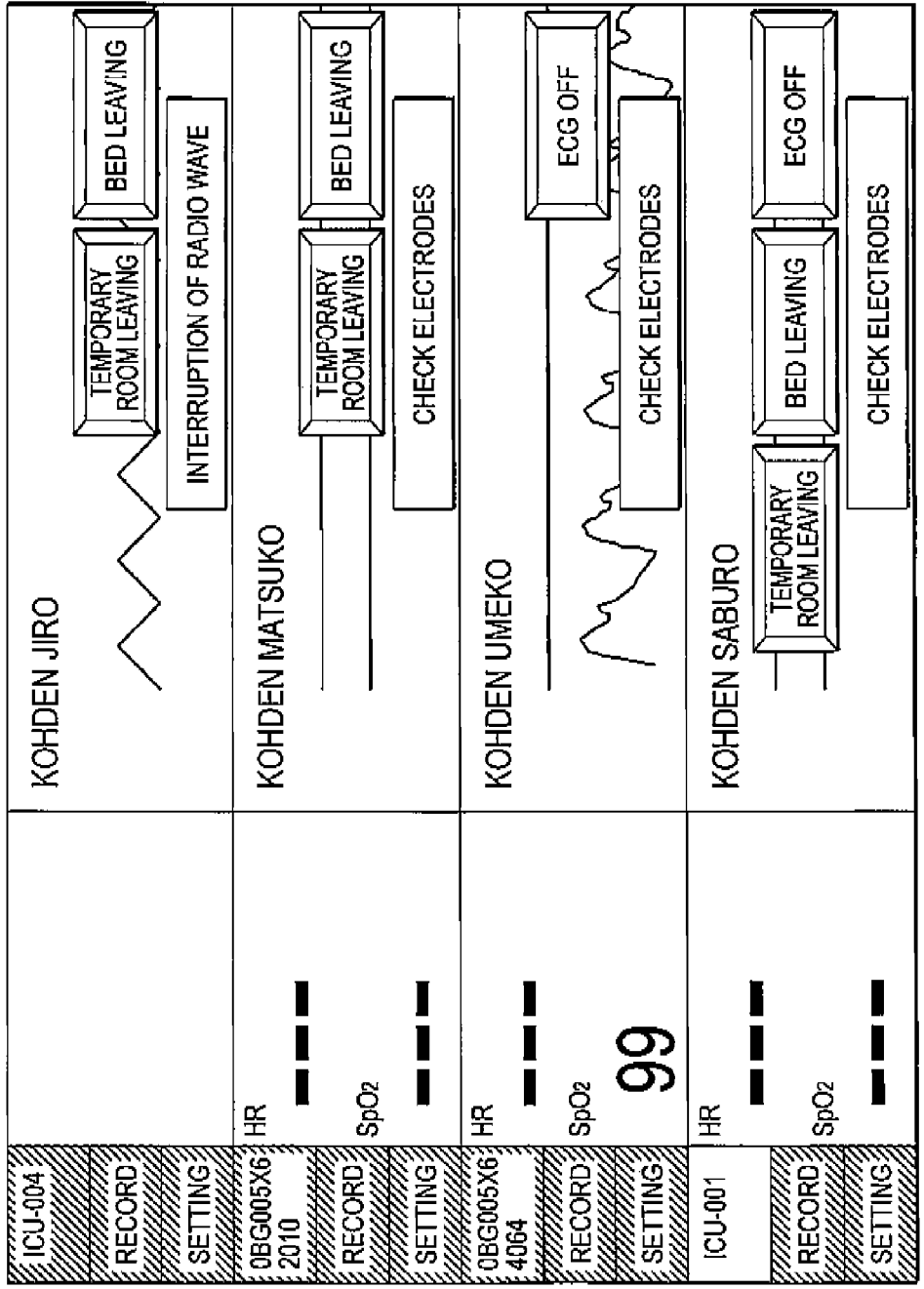
FIG. 14 is a view showing contents displayed on the displaying unit of the biological information monitoring apparatus, in the case where the pop-up navigation in the invention is displayed.

FIG. 14 shows a state where, in a similar manner as the above-described action message, further responding information of "TEMPORARY ROOM LEAVING", "BED LEAVING", and "ECG OFF" are displayed based on that at least one of conditions of the generation frequency, the generation number, the duration time, the integration time, and the like for the alarm is satisfied.

Here, "TEMPORARY ROOM LEAVING" is a setting which is used for suspending the measurement which is performed on the patient through the biological information monitoring apparatus, because of inspection. "BED LEAVING" is a setting which is used in the case where the measurement through the biological information monitoring apparatus is ended because, for example, the patient is discharged from the hospital. "ECG OFF" is a setting which is used in the case where the ECG measurement is unnecessary temporarily or permanently in accordance with the symptom severity or the like of the patient.

Figure 15:
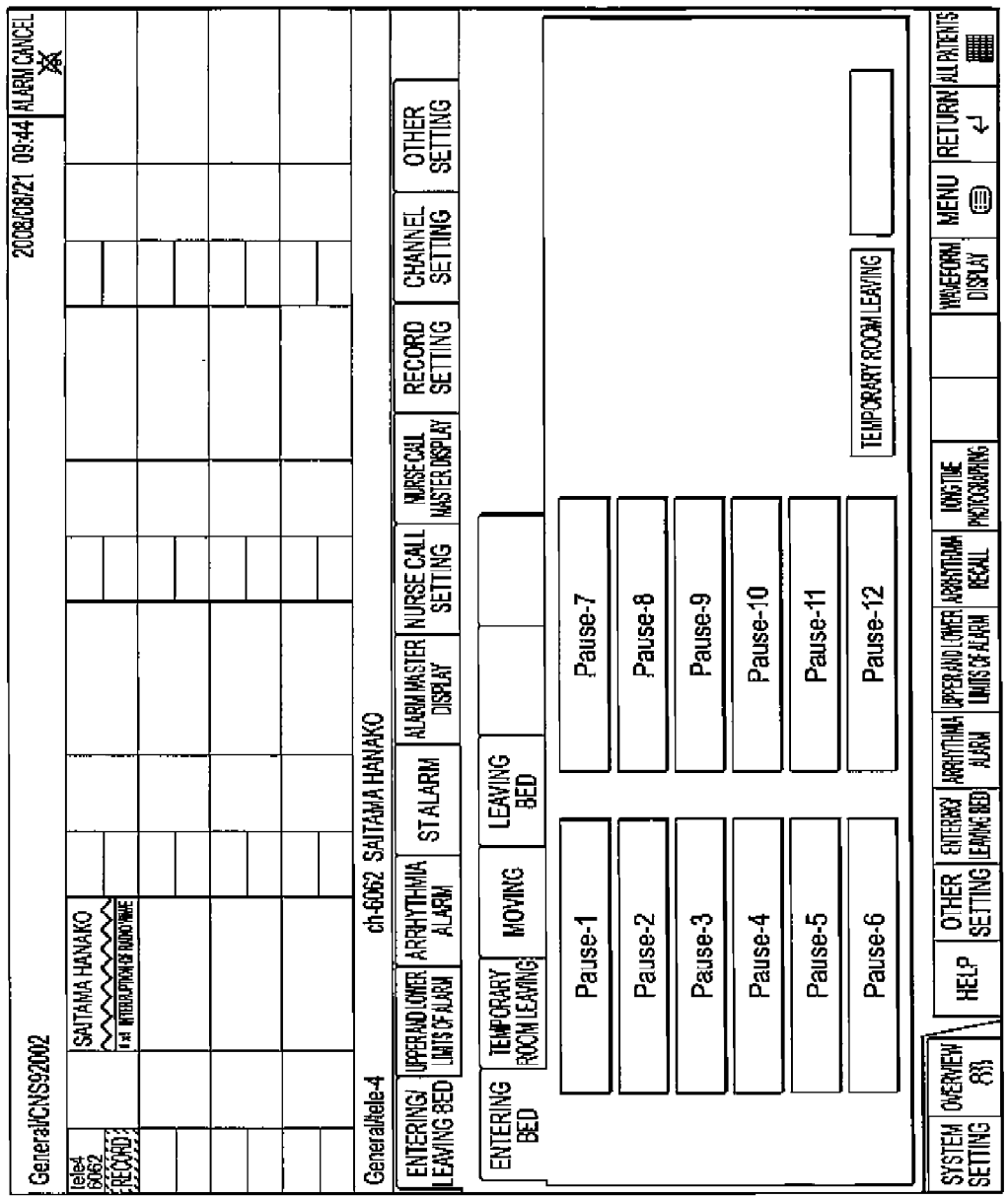
FIG. 15 is a view showing a screen for setting "TEMPORARY BED LEAVING" which is displayed on the displaying unit of the biological information monitoring apparatus, after a pop-up navigation of "TEMPORARY BED LEAVING" in the invention is pressed.
Figure 16:
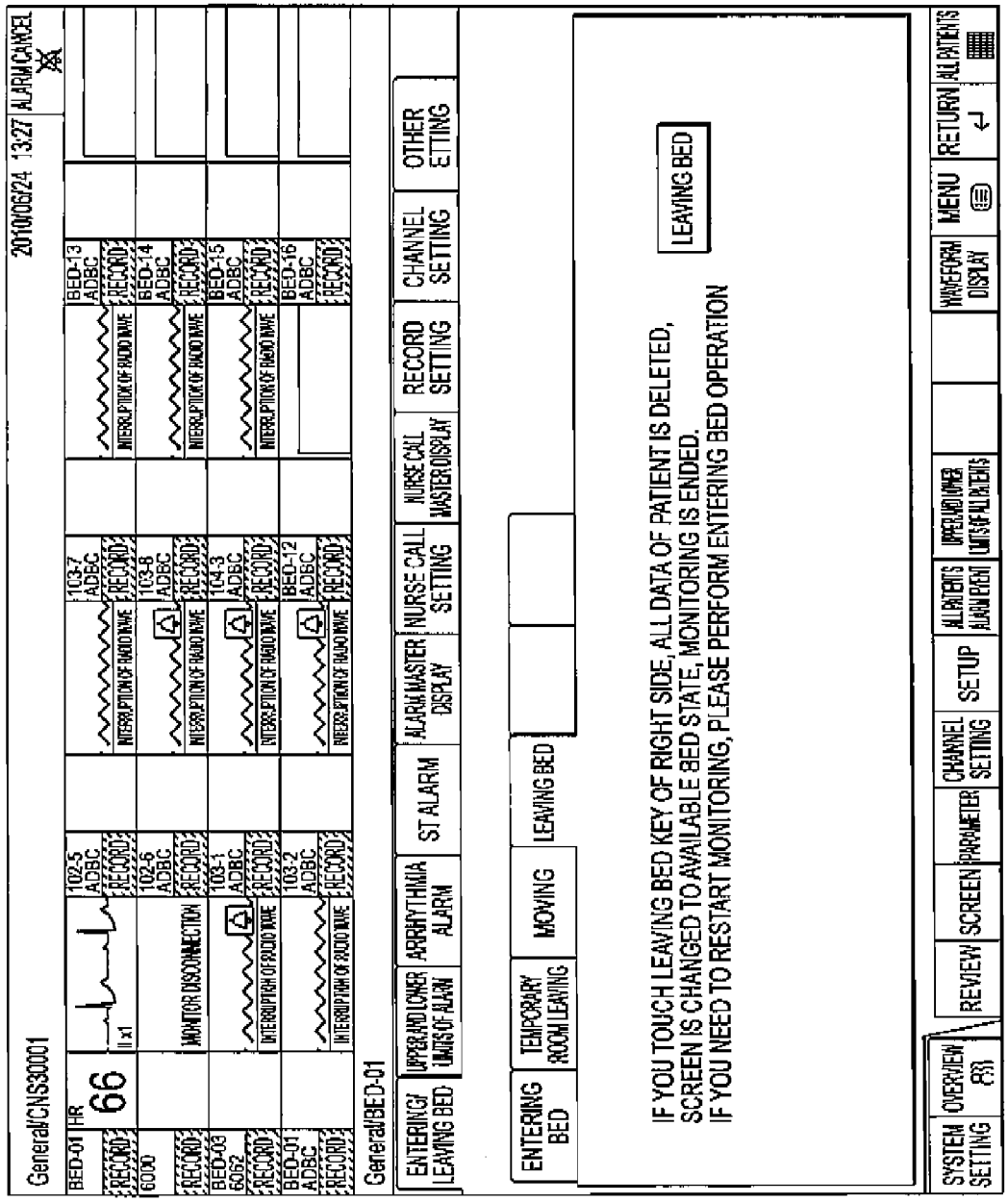
FIG. 16 is a view showing a screen for setting "ROOM LEAVING" which is displayed on the displaying unit of the biological information monitoring apparatus, after a pop-up navigation of "ROOM LEAVING" in the invention is pressed.
Figure 17:
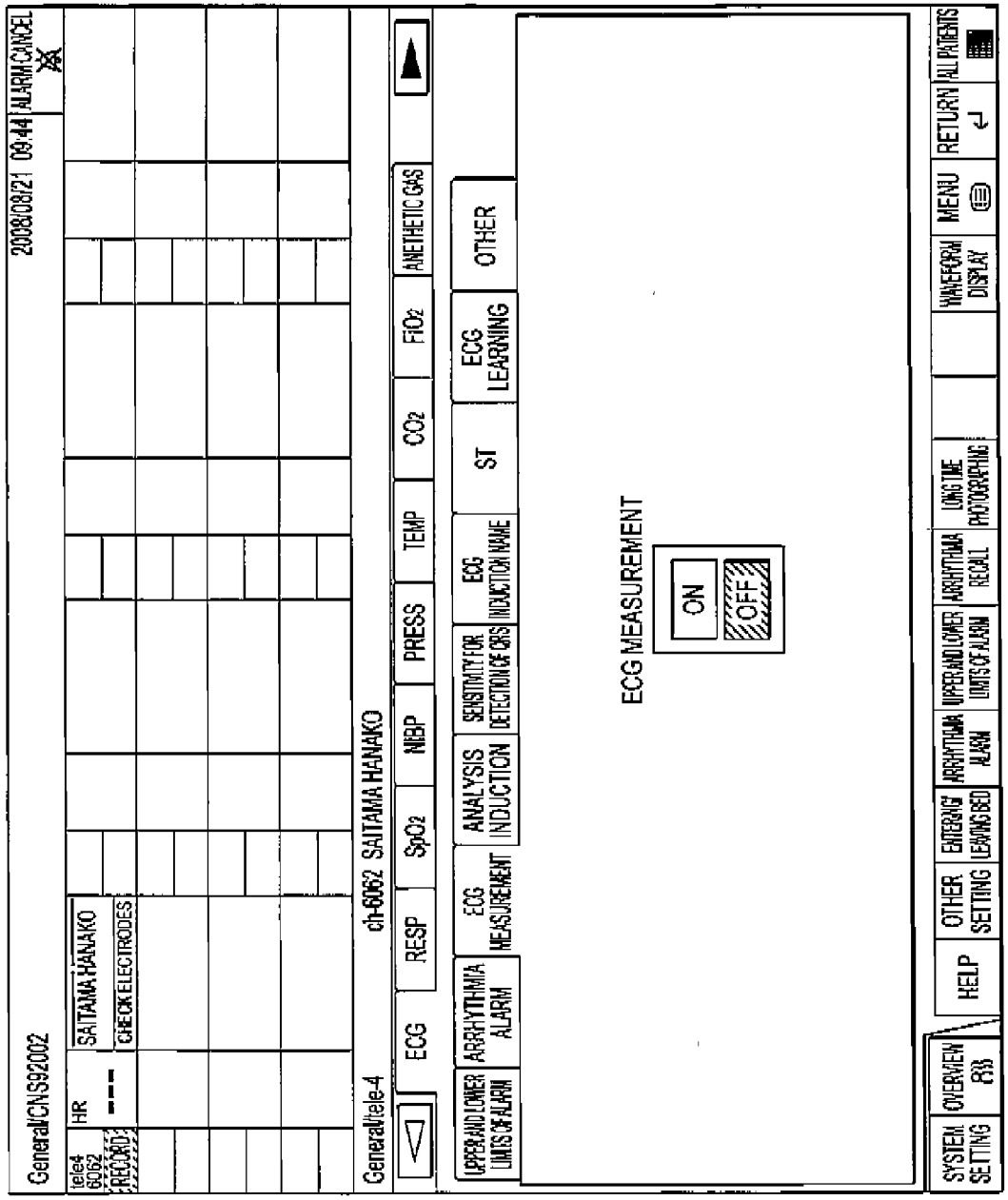
FIG. 17 is a view showing a screen for setting "ECG OFF" which is displayed on the displaying unit of the biological information monitoring apparatus, after a pop-up navigation of "ECG OFF" in the invention is pressed.

In a similar manner as the above-described guide key, "TEMPORARY ROOM LEAVING", "BED LEAVING", and "ECG OFF" shown in FIG. 14 are selectable (operable) by the user. When the user selects (clicks) one of them, one of the setting screens shown in FIGS. 15 to 17 is activated. When the user operates in accordance with the setting screen, the alarm is canceled.

With respect to KOHDEN Jiro, the alarm of "INTERRUPTION OF RADIO WAVE" is generated, and the alarm is continued for five minutes or longer. Therefore, "TEMPORARY ROOM LEAVING" and "BED LEAVING" which are seemed to be next operated by the user (or requested to be operated) are displayed.

With respect to all KOHDEN Matsuko, KOHDEN Umeko, and KOHDEN Saburo, the alarm of "CHECK ELECTRODES" is generated, and the alarm is continued for five minutes or longer. However, different sets of responding information are displayed for the three patients. This is an example showing that the responding information display controlling unit can determine further responding information which is to be displayed in accordance with respective states.

With respect to KOHDEN Matsuko, when the alarm of "CHECK ELECTRODES" is generated, the responding information display controlling unit detects that biological information such as the ECG and the pulse wave is not measured, and further responding information of "TEMPORARY ROOM LEAVING" and "BED LEAVING" is displayed.

With respect to KOHDEN Umeko, when the alarm of "CHECK ELECTRODES" is generated, the responding information display controlling unit detects that the ECG is not measured but other biological information such as the pulse wave is measured, "TEMPORARY ROOM LEAVING" and "BED LEAVING" are not displayed, but further responding information of "ECG OFF" is displayed.

With respect to KOHDEN Saburo, when the alarm of "CHECK ELECTRODES" is generated, the responding information display controlling unit fails to determine responding information to be displayed, and in this case all sets of possible further information are displayed.

As described above, further responding information to be displayed as the pop-up navigation may have a configuration which is determined by the responding information display controlling unit, or that which can be previously set by the user.

When the pop-up navigation of "TEMPORARY ROOM LEAVING" in FIG. 14 is pressed, the setting screen of "TEMPORARY ROOM LEAVING" shown in FIG. 15 is displayed on the displaying unit of the biological information monitoring apparatus.

When the pop-up navigation of "ROOM LEAVING" in FIG. 14 is pressed, the setting screen of "ROOM LEAVING" shown in FIG. 16 is displayed on the displaying unit of the biological information monitoring apparatus.

When the pop-up navigation of "ECG OFF" in FIG. 14 is pressed, the setting screen of "ECG" shown in FIG. 17 is displayed on the displaying unit of the biological information monitoring apparatus.

As described above, in the third example of the responding information in the invention, further responding information which corresponds to the generated alarm, and which is possibly next operated can be selectively acquired by a medical person, and an operation which is required for cancelling the alarm is expedited, whereby the alarm can be finally cancelled.

According to an aspect of the invention, a vital alarm that is output in abnormality of a detection signal, or a technical alarm that is output in abnormality of the biological information monitoring apparatus, a sensor, or the measurement environment is displayed on the displaying unit, and it is possible to display, after the vital alarm or the technical alarm is displayed, an action message or a guide screen as responding information that corresponds to the vital alarm or the technical alarm, or a pop-up navigation as further responding information, on the displaying unit.

When a vital alarm that is output in abnormality of a detection signal, or a technical alarm that is output in abnormality of the biological information monitoring apparatus, a sensor, or the measurement environment is displayed on the displaying unit, it is possible to output responding information in which a situation where a vital alarm or a technical alarm is generated in past is considered.

In the invention, it is possible to display an action message or a guide screen as responding information that corresponds to the vital alarm or the technical alarm, or a pop-up navigation as further responding information, on the displaying unit. Therefore, even an inexperienced medical person can respond the generated alarm without hesitation.

What is claimed is:

1. A biological information monitoring apparatus operable to receive biological information measured by a detector adapted to be attached to a patient, and operable to display the biological information on a display, the biological information monitoring apparatus comprising:
 a first display controller which displays an alarm on the display; and
 a second display controller which displays, on the display, responding information which responds to the displayed alarm, when a condition is satisfied.

2. The biological information monitoring apparatus according to claim 1, wherein the responding information includes means, instruction, or suggestion for canceling an abnormality related to the displayed alarm.

3. The biological information monitoring apparatus according to claim 1, wherein the alarm and the responding information are not superimposed on each other on the display.

4. The biological information monitoring apparatus according to claim 1, wherein the responding information includes at least one of a character and a graphical illustration.

5. The biological information monitoring apparatus according to claim 1, wherein when the responding information is displayed on the display, a sound is output.

6. The biological information monitoring apparatus according to claim 1, wherein the condition is a first condition that the displayed alarm satisfies at least one of predetermined conditions of a generation frequency, a generation number, a duration time, and an integration time.

7. The biological information monitoring apparatus according to claim 1, wherein when the condition is unsatisfied after the responding information is displayed, display of the responding information is cancelled.

8. The biological information monitoring apparatus according to claim 1, wherein satisfaction of the condition prompts a type of the alarm, and display of the responding information.

9. The biological information monitoring apparatus according to claim 1, wherein the responding information is displayed in a blinking or inverted manner.

10. The biological information monitoring apparatus according to claim 1, wherein the condition is a second condition that a user operates a guide key, which is displayed on the display at a time when the alarm is displayed, which is displayed on the display after a predetermined time elapses from a time when the alarm is displayed, or which is displayed on the display when a predetermined number of the alarm is reached.

11. The biological information monitoring apparatus according to claim 1, wherein the condition is a third condition that a user selects the alarm displayed on the display.

12. The biological information monitoring apparatus according to claim 1, wherein the responding information is formed by a window including a plurality of elements, and one of the plurality of elements which corresponds to the displayed alarm is displayed at a most forefront location on the display.

13. The biological information monitoring apparatus according to claim 1, wherein the condition is a first condition that the alarm satisfies at least one of predetermined conditions of a generation frequency, a generation number, a duration time, and an integration time, and the responding information is information which responds to the alarm and which a user can operate.

14. The biological information monitoring apparatus according to claim 13, wherein the information includes a plurality of information.

15. The biological information monitoring apparatus according to claim 13, wherein the second display controller determines the information to be displayed, based on presence or absence of the biological information to be measured.

16. The biological information monitoring apparatus according to claim 1, wherein the alarm includes at least one of a vital alarm that is output in abnormality of the biological information and a technical alarm that is output in abnormality of the biological information monitoring apparatus, the detector, or measurement environment.

17. A biological information monitoring apparatus operable to receive biological information measured by a detector adapted to be attached to a patient, and operable to display the biological information on a display, the biological information monitoring apparatus comprising:
 a first display controller which displays an alarm on the display in response to the biological information measured by the detector; and
 a second display controller which displays, on the display, responding information which responds to the displayed alarm, wherein the responding information displayed is determined based upon the biological information measured by the detector.

18. A biological information monitoring apparatus operable to receive biological information measured by a detector adapted to be attached to a patient, and operable to display the biological information on a display, the biological information monitoring apparatus comprising:
 a first display controller which displays an alarm on the display; and
 a second display controller which displays, on the display, responding information which responds to the displayed alarm, wherein the responding information displayed is determined based upon a combination of (i) biological information of a most recent alarm and (ii) biological information of at least one alarm previously displayed.

* * * * *